(12) United States Patent
Sparks et al.

(10) Patent No.: US 9,642,885 B2
(45) Date of Patent: May 9, 2017

(54) BLOOD PRESSURE REDUCTION WITH DIETARY SUPPLEMENTS

(71) Applicants: William S. Sparks, Bellaire, TX (US); Daryl L. De Luca, Sugar Land, TX (US); Denis R. De Luca, Fulshear, TX (US); Mark Houston, Franklin, TN (US)

(72) Inventors: William S. Sparks, Bellaire, TX (US); Daryl L. De Luca, Sugar Land, TX (US); Denis R. De Luca, Fulshear, TX (US); Mark Houston, Franklin, TN (US)

(73) Assignee: Biotics Research Corporation, Rosenberg, TX (US)

( * ) Notice: Subject to any disclaimer, the term of this patent is extended or adjusted under 35 U.S.C. 154(b) by 224 days.

(21) Appl. No.: 14/435,417

(22) PCT Filed: Oct. 16, 2012

(86) PCT No.: PCT/US2012/060446
§ 371 (c)(1),
(2) Date: Apr. 13, 2015

(87) PCT Pub. No.: WO2014/062165
PCT Pub. Date: Apr. 24, 2014

(65) Prior Publication Data
US 2015/0273007 A1    Oct. 1, 2015

(51) Int. Cl.
| | | |
|---|---|---|
| *A01N 65/00* | (2009.01) | |
| *A61K 36/87* | (2006.01) | |
| *A61K 36/85* | (2006.01) | |
| *A61K 31/185* | (2006.01) | |
| *A61K 31/375* | (2006.01) | |
| *A61K 31/4188* | (2006.01) | |
| *A61K 31/4415* | (2006.01) | |
| *A61K 31/593* | (2006.01) | |
| *A61K 33/06* | (2006.01) | |
| *A61K 9/00* | (2006.01) | |
| *A23L 33/105* | (2016.01) | |
| *A23L 33/15* | (2016.01) | |
| *A23L 33/155* | (2016.01) | |

(52) U.S. Cl.
CPC ........... *A61K 36/87* (2013.01); *A23L 33/105* (2016.08); *A23L 33/15* (2016.08); *A23L 33/155* (2016.08); *A61K 9/0053* (2013.01); *A61K 31/185* (2013.01); *A61K 31/375* (2013.01); *A61K 31/4188* (2013.01); *A61K 31/4415* (2013.01); *A61K 31/593* (2013.01); *A61K 33/06* (2013.01); *A61K 36/85* (2013.01); *A23V 2002/00* (2013.01)

(58) Field of Classification Search
CPC ...................................................... A61K 36/00
USPC ........................................................ 424/725
See application file for complete search history.

(56) References Cited

U.S. PATENT DOCUMENTS

| | | |
|---|---|---|
| 5,895,652 A | 4/1999 | Giampapa |
| 5,948,443 A | 9/1999 | Riley et al. |
| 6,649,195 B1 | 11/2003 | Gorsek |
| 6,733,797 B1 | 5/2004 | Summers |
| 7,651,707 B2 | 1/2010 | Kappagoda |
| 8,075,929 B2 | 12/2011 | Shrikhande et al. |
| 2002/0192303 A1 | 12/2002 | Arver et al. |
| 2004/0001817 A1 | 1/2004 | Giampapa |
| 2005/0112210 A1 | 5/2005 | Grossman et al. |
| 2006/0134300 A1 | 6/2006 | Newman |
| 2007/0184153 A1 | 8/2007 | Prasad et al. |
| 2008/0268095 A1 | 10/2008 | Herzog |

FOREIGN PATENT DOCUMENTS

| | | |
|---|---|---|
| CN | 102488052 | 6/2012 |
| JP | 2003212783 A | 7/2003 |
| JP | 2009510118 | 3/2009 |

OTHER PUBLICATIONS

Healthy Choice Naturals, Blood Pressure Formula, Label (2012).
Preuss et al "Protective Effects of a Novel Niacin Chromium-Bound Complex . . . " Ann. N.Y. Acad Sci 957: 250-259 (2002) US.
Al-Awwaddi et al "Extracts Enriched in Different Polyphenolic Families . . . " J Agric Food Chem (2005) 53, 151-157, American Chemical Soc. US.
Mohler, Emile et al., book, "Advanced Therapy in Hypertension and Vascular Disease" (2006) p. 722, BC Decker, publisher, Hamilton, ON, Canada.
Militante et al., "Treatment of hypertension with oral taurine, experimental and clinical studies" Amino Acids (2002) 23: 381-393, Springer-Verlag, Austria.

*Primary Examiner* — Michael Meller
(74) *Attorney, Agent, or Firm* — John R. Casperson

(57) ABSTRACT

A daily dose of 6,000 mg of taurine, 1,000 mg of vitamin C, 150 mg of grape seed extract, 100 mg of vitamin B6, 2 mg of biotin, 2,000 IU of vitamin D3, and 87 mg of magnesium is shown to reduce blood pressure in hypertensive individuals by more than 10 mm Hg.

6 Claims, 1 Drawing Sheet

BLOOD PRESSURE REDUCTION WITH DIETARY SUPPLEMENTS

TECHNICAL FIELD

In one aspect, this invention relates to the treatment of high blood pressure in humans with dietary supplements. In another aspect, this invention relates to compositions comprising combinations of known dietary supplements which are useful to treat hypertension when taken orally.

BACKGROUND ART

Multivitamins typically contain a large number of vitamins and minerals. Some of the ingredients can be harmful when taken in large amounts. For example, oil-soluble vitamins such as vitamin A or potentially toxic minerals such as selenium that are typically contained in multivitamins can be toxic at high doses. The potential toxicity of some of the components in multivitamins prevents a user of multivitamins from taking high enough multiples of daily multivitamins to receive any reduction in blood pressure that high doses of the components that modulate blood pressure might bestow. Also, multivitamins aren't formulated based on the capacity of the various ingredients to reduce blood pressure, and are lacking in ingredients known to reduce blood pressure but not categorized as essential vitamins and minerals.

Multisupplements that are not formulated for blood pressure reduction have similar shortcomings. Components that do not reduce blood pressure but are present in amounts that constitute a high percentage of a tolerable dose limit the total number of the multi-supplement tablets or capsules that can be safely taken in a day.

DISCLOSURE OF INVENTION

In a first embodiment of the invention, a dietary supplement composition is described as containing, as its major constituents, generally in the range of from about 50 to about 90 wt % taurine and in the range of from about 5 to about 45 wt % vitamin C, balance being generally no more than about 10% by weight and preferably no more than about 5% by weight, of at least one further constituent selected from the group consisting of grape seed extract, vitamin B6, biotin, vitamin D3, and magnesium, none of said further constituents being present in amounts of more than about 5% by weight, based on total weight of composition. An amount in the range of from about 2 to about 20 grams/day of this composition taken daily is effective to reduce blood pressure in a hypertensive individual.

In a second embodiment of the invention, a dietary supplement composition is provided characterized by from about 10 to about 100 parts by weight of taurine for each part by weight of powdered grape seed extract, and at least one additional component selected from the group consisting of vitamin C, vitamin B6, vitamin D3, biotin, and magnesium. The composition is useful for treating high blood pressure in a human by ingesting an amount in the range of about 2 to about 20 grams of the composition per day, preferably about 4 to about 12 grams per day. Based on the amount of grape seed extract, the composition is generally taken to as to provide an amount in the range of from about 50 to about 500 mg per day of grape seed extract.

In a third embodiment of the invention, a dietary supplement composition is characterized as consisting essentially of biotin, vitamin B6, vitamin D3, and at least one of plant flavonoid extract, vitamin C, and taurine. The composition comprises an amount in the range of from about 15 to about 100 mg of vitamin B6 for each mg of biotin and an amount in the range of from about 300 to about 2000 IU of vitamin D3 for each mg of biotin. The composition can be taken orally in an amount to provide in the range of from about 0.2 to about 4 mg of biotin per day to treat hypertension.

In a fourth embodiment of the invention, a dietary supplement composition is provided consisting essentially of vitamin C, vitamin B6, and at least one of plant flavonoid extract, biotin, taurine, vitamin D3 and magnesium. The composition generally comprises an amount in the range of from about 3 to about 20 mg of vitamin C for each mg of vitamin B6 and comprises in the range of from about 5 to about 45 weight percent of vitamin C, based on total weight of composition. To treat high blood pressure in humans, the composition can be taken in an amount to provide in the range of from about 300 to about 2000 mg of vitamin C per day.

BEST MODE FOR CARRYING OUT THE INVENTION

Figure 1:
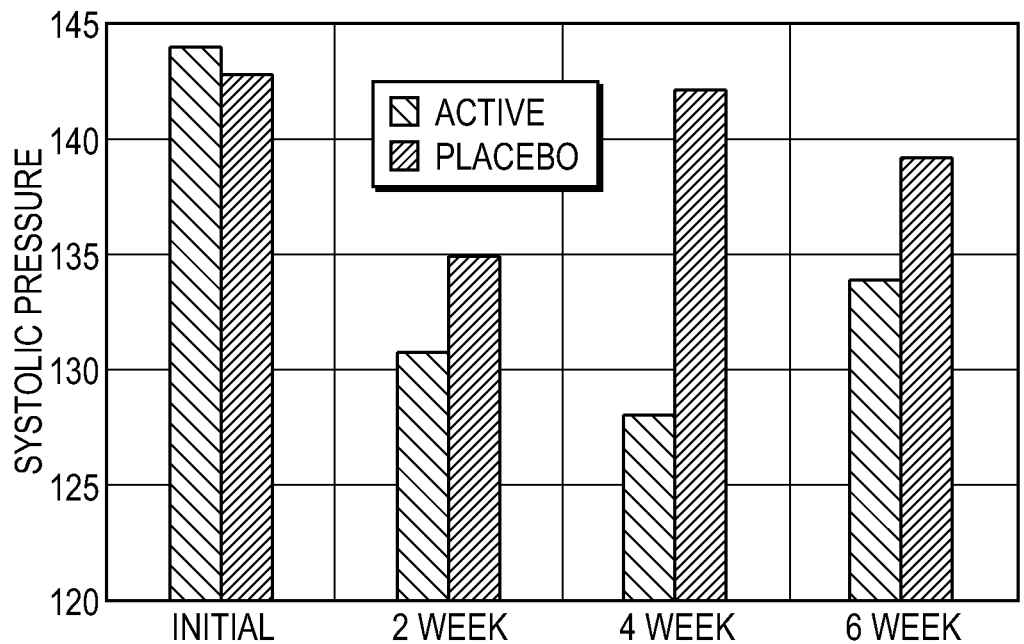
FIG. 1 is a bar chart comparing the effects on systolic blood pressure of ingesting active composition vs. placebo over a six week period.

The invention provides an orally-taken dietary supplement composition for treating hypertension in humans. By hypertension is meant a systolic reading in excess of 140 mm Hg or a diastolic reading in excess of 90 mm Hg. The invention can also be used to treat pre-hypertension in humans. By pre-hypertension is meant a systolic reading in excess of 130 or a diastolic reading in excess of 85 mm Hg. In tests on hypertensives, the invention was shown effective to reduce systolic and/or diastolic readings by 10 mm Hg or more. For treating hypertension or pre-hypertension, the treatment objective would be to reduce at least one, preferably both, of a patient's systolic and diastolic pressures to beneath the definitional limits.

A preferred dietary supplement composition according to an embodiment of the invention provides a daily dose of taurine, vitamin C, grape seed extract, vitamin B6, biotin, and vitamin D3 generally of in the range of
500 to 15,000 mg of taurine,
180 to 2,500 mg of vitamin C,
40 to 400 mg of plant flavonoid extract,
2 to 500 mg of vitamin B6,
0.05 to 5 mg of biotin, and
100 to 10,000 IU of vitamin D3.

Usually, the preferred dietary supplement composition provides daily doses in the range of
2,000 to 12,000 mg of taurine,
300 to 2,000 mg of vitamin C,
50 to 300 mg of grape seed extract,
30 to 200 mg of vitamin B6,
0.4 to 4 mg of biotin, and
600 to 4,000 IU of vitamin D3.

Preferably, the preferred dietary supplement composition provides daily doses in the range of
3,000 to 9,000 mg of taurine,
500 to 1,500 mg of vitamin C as magnesium ascorbate, 75 to 250 mg of grape seed extract comprising at least 50% by weight phenolics,
50 to 150 mg of vitamin B6,
1 to 3 mg of biotin, and
1,000 to 3,000 IU of vitamin D3.

An exemplary dietary supplement composition which was tested with good results provided a daily dose of
6,000 mg of taurine,
1,000 mg of vitamin C,
150 mg of grape seed extract,
100 mg of vitamin B6,
2 mg of biotin,
2,000 IU of vitamin D3, and
87 mg of magnesium.

The dietary supplement composition can be formulated for oral ingestion in a form selected from the group consisting of tablets, capsules, powders, liquids and gels. The amounts of the ingredient expressed herein are based on dry weight.

In a first embodiment of the invention, a dietary supplement composition is described as containing, as its major constituents, generally in the range of about 50 to about 90 wt % taurine and in the range of about 5 to about 45 wt % vitamin C, balance being generally no more than about 10% by weight and preferably no more than about 5% by weight, of at least one further constituent selected from the group consisting of grape seed extract, vitamin B6, biotin, vitamin D3, and magnesium, none of said further constituents being present in amounts of more than about 5% by weight, based on total weight of composition.

In a second embodiment of the invention, a dietary supplement composition is provided characterized by from about 10 to about 100 parts by weight of taurine for each part by weight of powdered grape seed extract, and at least one additional component selected from the group consisting of vitamin C, vitamin B6, vitamin D3, biotin, and magnesium. The composition is useful for treating high blood pressure in a human by orally ingestion of an amount in the range of from about 2 to about 20 grams of the composition per day, preferably in the range of from about 4 to about 12 grams per day. Based on the amount of grape seed extract, the composition is generally ingested in an amount to as to provide in the range of from about 50 to about 500 mg per day of grape seed extract.

The at least one additional component in the second embodiment of the invention usually comprises at least vitamin C. An amount in the range of about 2 to about 20 parts by weight of vitamin C for each part by weight of powdered grape seed extract is suitable. Preferably, the vitamin C is supplied in the form of magnesium ascorbate, in an amount of from about 4 to about 12 parts by weight of magnesium ascorbate for each part by weight of powdered grape seed extract.

Once serum levels of vitamin C are sufficient to promote stimulation of endothelial nitric oxide synthase activity, a dose of vitamin C about 180 mg/day may be suitable.

More preferably, the composition invention in the second embodiment of the invention further comprises from about 0.2 to about 1.3 parts by weight of vitamin B6 for each part by weight of powdered grape seed extract, from about 0.005 to about 0.03 parts by weight of biotin for each part by weight of powdered grape seed extract, and from about 4 to about 30 IU of vitamin D3 for each milligram by weight of powdered grape seed extract as the at least one additional component.

Magnesium, if present, preferably ranges from about 0.2 to 2 parts by weight for each part by weight of grape seed extract.

In a third embodiment of the invention, a dietary supplement composition is characterized as consisting essentially of biotin, vitamin B6, vitamin D3, and at least one of plant flavonoid extract, vitamin C, and taurine. The composition comprises in the range of from about 15 to about 100 mg of vitamin B6 for each mg of biotin and in the range of from about 300 to about 2000 IU of vitamin D3 for each mg of biotin.

To treat high blood pressure in humans, the just-described dietary supplement composition can be ingested in an amount to provide in the range of from about 0.2 to about 4 mg of biotin per day.

The composition in the third embodiment of the invention generally also contains plant flavonoid extract, generally grape seed extract and when it is present it is generally in an amount of from about 25 to about 150 mg for each mg of biotin. The composition usually also contains taurine and when it is present it is generally in an amount in the range of from about 1000 to about 6000 mg for each mg of biotin. The composition preferably also contains vitamin C and when it is present it is generally in an amount in the range of from about 150 to about 1000 mg for each mg of biotin. The composition preferably further contains magnesium in a biologically compatible form and when it is present it is generally in an amount of from about 15 to about 100 mg for each mg of biotin.

Typically, to treat hypertension, in the range of from about 2 to about 20 grams per day of the composition is ingested on a daily basis, preferably in an amount sufficient to reduce systolic blood pressure by at least 10 mm Hg.

In a fourth embodiment of the invention, a dietary supplement composition is provided consisting essentially of vitamin C, vitamin B6, and at least one of plant flavonoid extract, biotin, taurine, vitamin D3 and magnesium. The composition generally comprises in the range of from about 3 to about 20 mg of vitamin C for each mg of vitamin B6 and is constituted by in the range of from about 5 to about 45 weight percent of vitamin C, based on total weight of composition. Usually, the composition comprises taurine in an amount in the range of from about 50% to about 90% by weight, based on total weight of the composition. Preferably, the composition comprises detectable amounts of plant flavonoid extract, generally grape seed extract, biotin, vitamin D3 and magnesium in amounts of less than about 5% by weight, based on total weight of composition. The composition can be used to treat high blood pressure in humans. Generally speaking, an adequate amount of the composition is ingested to provide in the range of from about 300 to about 2000 mg of vitamin C per day. Where the composition further comprises magnesium, in the range of from about 30 to about 200 mg of magnesium per day is further provided. Where the composition further contains taurine, in the range of from about 2,000 to about 12,000 mg of taurine per day is further provided. Where the composition further comprises grape seed extract, in the range of from about 50 to about 300 mg of grape seed extract is provided per day. Where the composition further comprises vitamin B6, in the range of from about 30 to about 200 mg of vitamin B6 is provided per day. Where the composition further comprises biotin, in the range of from about 0.6 to about 4 mg of biotin is provided per day. Where the composition further comprises vitamin D3, in the range of from about 600 to about 4000 IU of vitamin D3 is provided per day.

The dietary supplement composition used in the study described hereinbelow provided 87 mg of magnesium daily which was obtained from the magnesium salt of ascorbic acid. Other forms of magnesium in a biologically compatible form could be used such as but not limited to magnesium oxide, magnesium sulfate, magnesium chloride, amino acid chelates of magnesium, magnesium carbonate, magnesium citrate, magnesium gluconate, magnesium malate.

Pyridoxine HCl was the form of vitamin B6 used in the study. Other forms of vitamin B6 which would be effective include pyridoxal 5 phosphate and pyridoxine alpha ketoglutarate.

The grape seed extract used in the study below was generally prepared as described in U.S. Pat. No. 7,651,707, the disclosure of which is incorporated by reference. However, the extract need not conform to the specifications described in U.S. Pat. No. 7,651,707 in order to be used in accordance with the invention. The extract used in the study contains a variety of phenolic compounds including epticatechin-gallate, monomers, dimers, trimers, tetramers and pentamers. It is not known which compound or group of compounds contributes to the reduction of blood pressure. However, it is known that many plant derived flavonoid type compounds can stimulate the release of endothelial derived nitric oxide (NO), which is known to cause vasodilation and a reduction in blood pressure. We selected a plant flavonoid extract with reported effects on stimulating NO release from endothelial cells. Other extracts from pine bark, chocolate, black and green teas have been reported to increase endothelial NO. The preferred extract would be from grape seed but it would not necessarily have to conform to the specifications of U.S. Pat. No. 7,651,707.

EXAMPLE

A study was conducted to assess the effects of carrying out the invention.

To be part of the study design a patient had to have a blood pressure reading of 140 mm Hg or more systolic pressure and/or diastolic pressure of 90 mm Hg or more. This reading conforms to the definition of arterial hypertension (formally known as essential hypertension). Patients that had been taking blood pressure medicine had to washout (discontinue using blood pressure medicines) for a period of one month before being selected for the study. Patients were screened at a medical clinic to qualify for the study. The clinic was blinded in the study. The patients and the health care providers were given identically labeled bottles that either contained the actives or a placebo. Blood pressure values were obtained as an average of three blood pressure readings recorded by a medical nurse. Patients were required to be measured every two weeks at the clinic. If a patient reported illness (feeling ill, having cold or flu-like symptoms, or migraine) data was not reported. Patients were informed not to make any life style changes such as smoking, coffee, etc) during the study. Two lot numbers were used in the study to identify placebo or active. Patients continued on the same lot number during the study. Twenty two patients were given the active product. Measurements were made on all 22 patients at week two, 17 of the 22 patients at week four and 7 patients of the 22 at week 6. The placebo group began with 20 patients. 17 placebo patients were measured at week two (three dropped out of the study). 16 of the 17 were measured at week four. 13 of 17 were measured at week six. The main reasons for dropping out of study were running out of product, not coming back to the clinic to be tested, or illness.

The dietary supplement composition that was tested in the study was supplied as a mixed powder that was taken once daily. The powder contained, as a single daily dose: (1) magnesium ascorbate (supplying 1000 mg of ascorbic acid and 87 mg of magnesium as a fully buffered salt of magnesium and ascorbic acid (vitamin C)), (2) pyridoxine HCl, providing 100 mg of vitamin B6, (3) taurine 6 grams, (4) biotin 2 mg, (5) vitamin D3 2000 international units and (6) grape seed extract 150 mg. The powder was dispensed by using a 9 cc scoop supplying 7.8 grams of product per day.

FIG. 1 compares the observed mean systolic blood pressure (mm of Hg) of the active group to the placebo group at weeks 0, 2, 4 and 6. The active group had a lower mean systolic blood pressure than the placebo group at weeks 2, 4 and 6. The mean improvement for the active group from baseline was −14 mm at week 2, −15 mm at week 4, and −12 mm at week 6. Compared to mean from the placebo group, the mean improvement was −4 mm at week 2, −14 mm at week 4, −5 mm at week 6.

Figure 2:
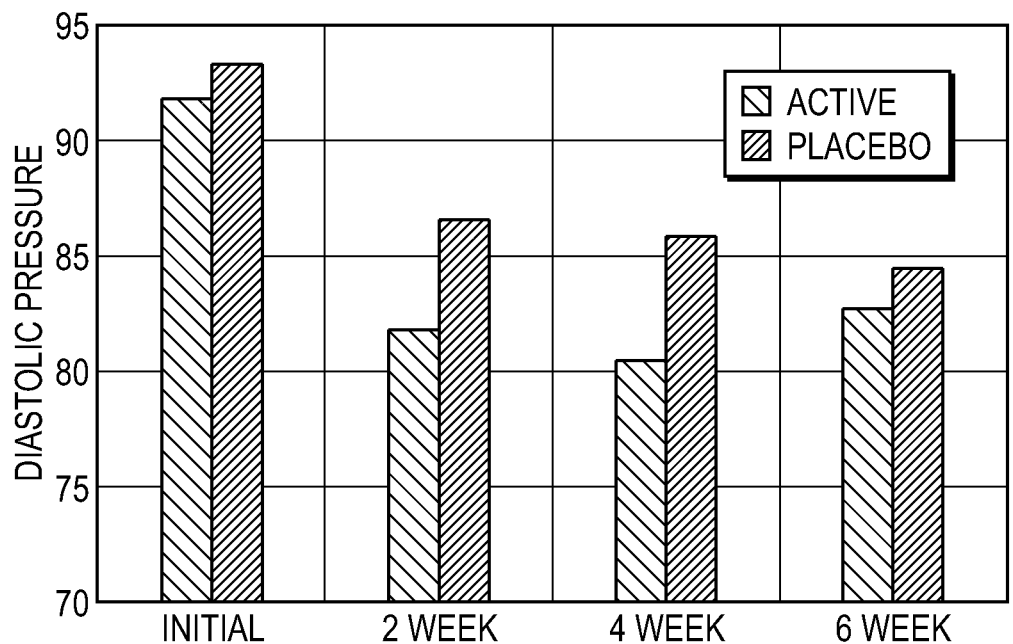
FIG. 2 is a bar chart comparing the effects on diastolic blood pressure of ingesting active composition vs. placebo over a six week period.

FIG. 2 compares the observed mean diastolic blood pressure (mm of Hg) of the active group to the placebo group at weeks 0, 2, 4 and 6. The active group had a lower mean diastolic blood pressure than the placebo group at weeks 2, 4 and 6. The mean improvement for the active group from baseline was −10 mm at week 2, −11 mm at week 4, and −9 mm at week 6. Compared to the mean from the placebo group, the mean improvement was −5 mm at week 2, −5 mm at week 4, −2 mm at week 6.

The invention claimed is:

1. A method for treating high blood pressure in a human in need thereof consisting essentially of administering to said human in need thereof taurine, magnesium ascorbate, grape seed extract, pyridoxine hydrochloride, biotin, and cholecalciferol, wherein said human in need thereof is administered from about 3,000 to about 12,000 mg of taurine per day, from about 300 mg to about 2000 mg of magnesium ascorbate per day, from about 50 mg to about 300 mg of grape seed extract per day, from about 2 mg to about 500 mg of pyridoxine hydrochloride per day, from about 0.6 mg to about 4 mg of biotin per day, and from about 600 IU to about 4000 IU of cholecalciferol per day.

2. The method of claim 1, wherein said grape seed extract is administered at 25-150 mg for each mg of biotin.

3. The method of claim 1, wherein said human when treated with the composition is able to maintain a systolic blood pressure in the human of less than 140 mm Hg.

4. A method of treating hypertension in a human in need thereof consisting essentially of administering to a human in need thereof therapeutically effective amounts of a grape seed extract, magnesium ascorbate, cholecalciferol, biotin, taurine, and pyridoxine hydrochloride.

5. A method as in claim 4, wherein the therapeutically effective amounts are:
50 to 500 mg of grape seed extract per day,
300 to 2,000 mg of magnesium ascorbate per day,
600 to 4,000 IU of cholecalciferol 0.4 to 4 mg of biotin per day,
2,000 to 12,000 mg of taurine per day, and
30 to 200 mg of pyridoxine hydrochloride per day.

6. A method as in claim 4, wherein the therapeutically effective amounts are:
75 mg to 250 mg of grape seed extract per day,
500 mg to 1,500 mg of magnesium ascorbate per day,
1,000 IU to 3,000 IU of cholecalciferol per day,
1 mg to 3 mg of biotin per day,
3,000 mg to 9,000 mg of taurine per day, and
50 mg to 150 mg of pyridoxine hydrochloride per day.

* * * * *